(12) United States Patent
Hossainy

(10) Patent No.: US 7,115,300 B1
(45) Date of Patent: Oct. 3, 2006

(54) METHOD OF COATING IMPLANTABLE MEDICAL DEVICES

(75) Inventor: Syed F. A. Hossainy, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 169 days.

(21) Appl. No.: 10/772,858

(22) Filed: Feb. 4, 2004

Related U.S. Application Data

(63) Continuation-in-part of application No. 10/040,574, filed on Dec. 28, 2001, now Pat. No. 6,709,514.

(51) Int. Cl.
*B05D 3/12* (2006.01)

(52) U.S. Cl. .................. 427/2.24; 427/2.25; 427/240

(58) Field of Classification Search .............. None
See application file for complete search history.

(56) References Cited

U.S. PATENT DOCUMENTS

| | | | |
|---|---|---|---|
| 3,288,052 A | 11/1966 | Hough | 99/235 |
| 4,148,932 A | 4/1979 | Tada et al. | 427/31 |
| 4,275,838 A | 6/1981 | Fangmeyer | 239/223 |
| 4,329,383 A | 5/1982 | Joh | 428/36 |
| 4,589,597 A | 5/1986 | Robisch et al. | 239/703 |
| 4,684,064 A | 8/1987 | Kwok | 239/223 |
| 4,733,665 A | 3/1988 | Palmaz | 128/343 |
| 4,795,095 A | 1/1989 | Shepard | 239/214.17 |
| 4,800,882 A | 1/1989 | Gianturco | 128/343 |
| 4,882,168 A | 11/1989 | Casey et al. | 424/468 |
| 4,886,062 A | 12/1989 | Wiktor | 128/343 |
| 4,927,081 A | 5/1990 | Kwok et al. | 239/223 |
| 4,941,870 A | 7/1990 | Okada et al. | 600/36 |
| 4,977,901 A | 12/1990 | Ofstead | 128/772 |
| 5,112,457 A | 5/1992 | Marchant | 204/165 |
| 5,165,919 A | 11/1992 | Sasaki et al. | 424/488 |
| 5,272,012 A | 12/1993 | Opolski | 428/423.1 |
| 5,292,516 A | 3/1994 | Viegas et al. | 424/423 |
| 5,298,260 A | 3/1994 | Viegas et al. | 424/486 |
| 5,300,295 A | 4/1994 | Viegas et al. | 424/427 |
| 5,306,501 A | 4/1994 | Viegas et al. | 424/423 |
| 5,328,471 A | 7/1994 | Slepian | 604/101 |
| 5,330,768 A | 7/1994 | Park et al. | 424/501 |
| 5,380,299 A | 1/1995 | Fearnot et al. | 604/265 |
| 5,399,198 A | 3/1995 | Ghaisas | 118/629 |
| 5,417,981 A | 5/1995 | Endo et al. | 424/486 |
| 5,447,724 A | 9/1995 | Helmus et al. | 424/426 |
| 5,455,040 A | 10/1995 | Marchant | 424/426 |
| 5,462,990 A | 10/1995 | Hubbell et al. | 525/54.1 |
| 5,464,650 A | 11/1995 | Berg et al. | 427/2.3 |
| 5,569,463 A | 10/1996 | Helmus et al. | 424/426 |
| 5,578,073 A | 11/1996 | Haimovich et al. | 623/1 |

(Continued)

FOREIGN PATENT DOCUMENTS

EP    0 301 856    2/1989

(Continued)

OTHER PUBLICATIONS

Anonymous, *Cardiologists Draw—Up The Dream Stent*, Clinica 710:15 (Jun. 17, 1996), http://www.dialogweb.com/cgi/document?req=1061848202959, printed Aug. 25, 2003 (2 pages).

(Continued)

*Primary Examiner*—Erma Cameron
(74) *Attorney, Agent, or Firm*—Squire, Sanders & Dempsey L.L.P.

(57) ABSTRACT

A method of coating a medical device, such as a stent is provided.

12 Claims, 3 Drawing Sheets

U.S. PATENT DOCUMENTS

| | | | |
|---|---|---|---|
| 5,605,696 A | 2/1997 | Eury et al. | 424/423 |
| 5,609,629 A | 3/1997 | Fearnot et al. | 623/1 |
| 5,624,411 A | 4/1997 | Tuch | 604/265 |
| 5,628,730 A | 5/1997 | Shapland et al. | 604/21 |
| 5,649,977 A | 7/1997 | Campbell | 623/1 |
| 5,658,995 A | 8/1997 | Kohn et al. | 525/432 |
| 5,667,767 A | 9/1997 | Greff et al. | 424/9.411 |
| 5,670,558 A | 9/1997 | Onishi et al. | 523/112 |
| 5,679,400 A | 10/1997 | Tuch | 427/2.14 |
| 5,700,286 A | 12/1997 | Tartaglia et al. | 623/1 |
| 5,702,754 A | 12/1997 | Zhong | 427/2.12 |
| 5,716,981 A | 2/1998 | Hunter et al. | 514/449 |
| 5,735,897 A | 4/1998 | Buirge | 623/12 |
| 5,746,998 A | 5/1998 | Torchilin et al. | 424/9.4 |
| 5,776,184 A | 7/1998 | Tuch | 623/1 |
| 5,788,979 A | 8/1998 | Alt et al. | 424/426 |
| 5,800,392 A | 9/1998 | Racchini | 604/96 |
| 5,820,917 A | 10/1998 | Tuch | 427/2.1 |
| 5,824,048 A | 10/1998 | Tuch | 623/1 |
| 5,824,049 A | 10/1998 | Ragheb et al. | 623/1 |
| 5,830,178 A | 11/1998 | Jones et al. | 604/49 |
| 5,837,008 A | 11/1998 | Berg et al. | 623/1 |
| 5,837,313 A | 11/1998 | Ding et al. | 427/2.21 |
| 5,851,508 A | 12/1998 | Greff et al. | 424/9.411 |
| 5,858,746 A | 1/1999 | Hubbell et al. | 435/177 |
| 5,865,814 A | 2/1999 | Tuch | 604/265 |
| 5,869,127 A | 2/1999 | Zhong | 427/2.12 |
| 5,873,904 A | 2/1999 | Ragheb et al. | 623/1 |
| 5,876,433 A | 3/1999 | Lunn | 623/1 |
| 5,877,224 A | 3/1999 | Brocchini et al. | 514/772.2 |
| 5,925,720 A | 7/1999 | Kataoka et al. | 525/523 |
| 5,955,509 A | 9/1999 | Webber et al. | 514/772.7 |
| 5,957,974 A | 9/1999 | Thompson et al. | 623/1.13 |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 5,997,517 A | 12/1999 | Whitbourne | 604/265 |
| 6,010,530 A | 1/2000 | Goicoechea | 623/1 |
| 6,015,541 A | 1/2000 | Greff et al. | 424/1.25 |
| 6,033,582 A | 3/2000 | Lee et al. | 216/37 |
| 6,042,875 A | 3/2000 | Ding et al. | 427/2.24 |
| 6,045,864 A | 4/2000 | Lyons et al. | 427/255.23 |
| 6,051,576 A | 4/2000 | Ashton et al. | 514/255 |
| 6,051,648 A | 4/2000 | Rhee et al. | 525/54.1 |
| 6,056,993 A | 5/2000 | Leidner et al. | 427/2.25 |
| 6,060,451 A | 5/2000 | DiMaio et al. | 514/13 |
| 6,060,518 A | 5/2000 | Kabanov et al. | 514/781 |
| 6,080,488 A | 6/2000 | Hostettler et al. | 428/423.3 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,110,483 A | 8/2000 | Whitbourne et al. | 424/423 |
| 6,113,629 A | 9/2000 | Ken | 623/1.1 |
| 6,120,536 A | 9/2000 | Ding et al. | 623/1.43 |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,153,252 A | 11/2000 | Hossainy et al. | 427/2.3 |
| 6,165,212 A | 12/2000 | Dereume et al. | 623/1.13 |
| 6,189,804 B1 | 2/2001 | Vetter et al. | 239/7 |
| 6,203,551 B1 | 3/2001 | Wu | 606/108 |
| 6,231,600 B1 | 5/2001 | Zhong | 623/1.42 |
| 6,240,616 B1 | 6/2001 | Yan | 29/527.2 |
| 6,245,753 B1 | 6/2001 | Byun et al. | 514/56 |
| 6,251,136 B1 | 6/2001 | Guruwaiya et al. | 623/1.46 |
| 6,254,632 B1 | 7/2001 | Wu et al. | 623/1.15 |
| 6,258,121 B1 | 7/2001 | Yang et al. | 623/1.46 |
| 6,267,073 B1 | 7/2001 | Busse et al. | 118/24 |
| 6,283,947 B1 | 9/2001 | Mirzaee | 604/264 |
| 6,283,949 B1 | 9/2001 | Roorda | 604/288.02 |
| 6,284,305 B1 | 9/2001 | Ding et al. | 427/2.28 |
| 6,287,628 B1 | 9/2001 | Hossainy et al. | 427/2.3 |
| 6,299,604 B1 | 10/2001 | Ragheb et al. | 604/265 |
| 6,306,176 B1 | 10/2001 | Whitbourne | 623/23.59 |
| 6,331,313 B1 | 12/2001 | Wong et al. | 424/427 |
| 6,335,029 B1 | 1/2002 | Kamath et al. | 424/423 |
| 6,346,110 B1 | 2/2002 | Wu | 606/108 |
| 6,358,556 B1 | 3/2002 | Ding et al. | 427/2.24 |
| 6,379,381 B1 | 4/2002 | Hossainy et al. | 623/1.42 |
| 6,395,326 B1 | 5/2002 | Castro et al. | 427/2.24 |
| 6,419,692 B1 | 7/2002 | Yang et al. | 623/1.15 |
| 6,451,373 B1 | 9/2002 | Hossainy et al. | 427/2.25 |
| 6,494,862 B1 | 12/2002 | Ray et al. | 604/96.01 |
| 6,503,556 B1 | 1/2003 | Harish et al. | 427/2.24 |
| 6,503,954 B1 | 1/2003 | Bhat et al. | 514/772.2 |
| 6,506,437 B1 | 1/2003 | Harish et al. | 427/2.25 |
| 6,527,801 B1 | 3/2003 | Dutta | 623/1.46 |
| 6,527,863 B1 | 3/2003 | Pacetti et al. | 118/500 |
| 6,540,776 B1 | 4/2003 | Sanders Millare et al. | 623/1.15 |
| 6,544,223 B1 | 4/2003 | Kokish | 604/103.01 |
| 6,544,543 B1 | 4/2003 | Mandrusov et al. | 424/422 |
| 6,544,582 B1 | 4/2003 | Yoe | 427/2.24 |
| 6,555,157 B1 | 4/2003 | Hossainy | 427/2.24 |
| 6,558,733 B1 | 5/2003 | Hossainy et al. | 427/2.25 |
| 6,565,659 B1 | 5/2003 | Pacetti et al. | 118/500 |
| 6,572,644 B1 | 6/2003 | Moein | 623/1.11 |
| 6,585,765 B1 | 7/2003 | Hossainy et al. | 623/1.45 |
| 6,585,926 B1 | 7/2003 | Mirzaee | 264/400 |
| 6,605,154 B1 | 8/2003 | Villareal | 118/500 |
| 6,663,662 B1 * | 12/2003 | Pacetti et al. | 623/1.13 |
| 6,783,793 B1 * | 8/2004 | Hossainy et al. | 427/2.25 |
| 2001/0018469 A1 | 8/2001 | Chen et al. | 523/121 |
| 2001/0037145 A1 | 11/2001 | Guruwaiya et al. | 623/1.15 |
| 2002/0077693 A1 | 6/2002 | Barclay et al. | 623/1.13 |
| 2002/0091433 A1 | 7/2002 | Ding et al. | 623/1.2 |
| 2002/0155212 A1 | 10/2002 | Hossainy | 427/2.25 |
| 2003/0065377 A1 | 4/2003 | Davila et al. | 623/1.13 |
| 2003/0099712 A1 | 5/2003 | Jayaraman | 424/486 |

FOREIGN PATENT DOCUMENTS

| | | |
|---|---|---|
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 273 314 | 1/2003 |
| JP | 2001-190687 | 7/2001 |
| WO | WO 91/12846 | 9/1991 |
| WO | WO 95/10989 | 4/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/17331 | 4/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |

| | | |
|---|---|---|
| WO | WO 01/15751 | 3/2001 |
| WO | WO 01/17577 | 3/2001 |
| WO | WO 01/37892 * | 5/2001 |
| WO | WO 01/45763 | 6/2001 |
| WO | WO 01/49338 | 7/2001 |
| WO | WO 01/74414 | 10/2001 |
| WO | WO 02/03890 | 1/2002 |
| WO | WO 02/026162 | 4/2002 |
| WO | WO 02/34311 | 5/2002 |
| WO | WO 02/056790 | 7/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |

OTHER PUBLICATIONS

Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cqui/document?req=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catherization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-1999 (1998).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials For Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694(1996).

Shigeno, *Prevention of Cerebrovascular Spasm By Bosentan, Novel Endothelin Receptor*; Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

* cited by examiner

METHOD OF COATING IMPLANTABLE MEDICAL DEVICES

CROSS REFERENCE

This application is a continuation-in-part of U.S. Pat. No. 6,709,514, application Ser. No. 10/040,574 filed on Dec. 28, 2001.

BACKGROUND OF THE INVENTION

1. Field of the Invention

This invention relates to a method for coating implantable medical devices, such as stents.

2. Description of the Background

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially press against the atherosclerotic plaque of the lesion for remodeling of the vessel wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Vasospasms and recoil of the vessel wall also threaten vessel closure. Moreover, thrombosis and restenosis of the artery can develop over several months after the procedure, which can require another angioplasty procedure or a surgical by-pass operation. To reduce the partial or total occlusion of the artery by the collapse of arterial lining and to reduce the chance of the development of thrombosis and restenosis, a stent is implanted in the lumen to maintain the vascular patency.

Stents can be used not only as a mechanical intervention but also as a vehicle for providing biological therapy. As a mechanical intervention, stents can act as scaffoldings, functioning to physically hold open and, if desired, to expand the wall of the passageway. Typically stents are capable of being compressed, so that they can be inserted through small lumens via catheters, and then expanded to a larger diameter once they are at the desired location.

Although stents work well mechanically, the chronic issues of restenosis and, to a lesser extent, thrombosis remain. These events are adversely affected by the mechanical aspects of the stent such as the degree of injury and disturbance in hemodynamics caused by the stent. To the extent that the mechanical functionality of stents has been optimized, it has been postulated that continued improvements could be made by pharmacological therapies. Many systemic therapies have been tried. A challenge is maintaining the necessary concentration of a therapeutic substance at the lesion site for the necessary period of time. This can be done via brute force methods using oral or intravenous administration but the issues of systemic toxicity and side effects arise. Therefore, a preferred route can be achieved by local delivery of a therapeutic substance from the stent itself. Being made of metal, plain stents are not useful for therapeutic substance delivery. Therefore, a coating, usually made from a polymer, is applied to serve as a therapeutic substance reservoir. A solution of a polymer dissolved in a solvent and a therapeutic substance added thereto is applied to the stent and the solvent is allowed to evaporate. Accordingly, a polymeric coating impregnated with a therapeutic substance remains on the surface of the stent. The polymeric coating can include multiple layers. A primer composition, free from any drugs, can be applied on the surface of the device. A polymer solution including the drug can then be applied on the primer layer. To reduce the rate of release of the drug, a topcoat layer can be applied over the reservoir layer. The application of each layer can be performed subsequent to the drying of the previous layer.

In order to be effectively applied with conventional spraying or dipping techniques, the coating solution needs to have a low viscosity. Low viscosities can be achieved by adding a higher fraction of solvent to the solution or by changing the composition of the solution with the addition of a "wetting fluid." Compositions having a low viscosity require multiple applications of the composition and evaporation of the solvent in order to obtain a coating of suitable thickness or weight, as compared to using compositions having greater viscosities. Accordingly, it is desired to use more viscous compositions to reduce the number of application steps and in effect reduce the processing time of forming the coating.

The topcoat layer is intended to reduce the rate of release of the drug from the polymer-drug layer. However, when a topcoat composition is applied to the polymer-drug layer, the solvent may extract the drug out from the polymer-drug layer, therefore reducing the effectiveness of the topcoat layer. Accordingly, it is desired to prevent the extraction of the drug out from the drug-polymer layer when a top coat layer is applied.

SUMMARY OF THE INVENTION

In accordance with one aspect of the invention, a method for coating an implantable medical device is provided, comprising forming a polymer layer containing a drug on the device, and applying a polymer melt free from any solvents to the polymer layer to form a topcoat layer.

In accordance with another aspect of the invention, a method of coating an implantable medical device is provided, comprising applying a coating material to a disk member and spinning the disk member about an axis of the disk member such that the force that is applied to the coating material by the disk member discharges the coating material off of the disk member and onto the device.

In accordance with another aspect of the invention, a method for coating an implantable medical device is provided, comprising forming a polymer layer containing a drug on the device, applying a polymer in a liquid state and free from any solvents to the polymer layer to form a topcoat layer, wherein the during the application of the topcoat layer the migration of the drug from the polymer layer is prevented or significantly minimized.

DETAILED DESCRIPTION

Figure 1A:
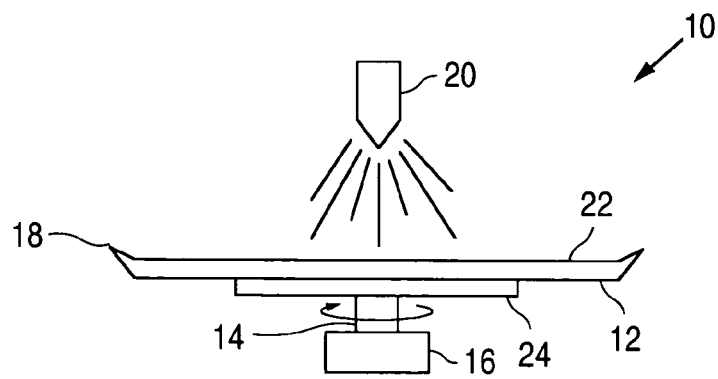
FIGS. 1A–1E illustrate various embodiments of the coating apparatus.
Figure 1B:
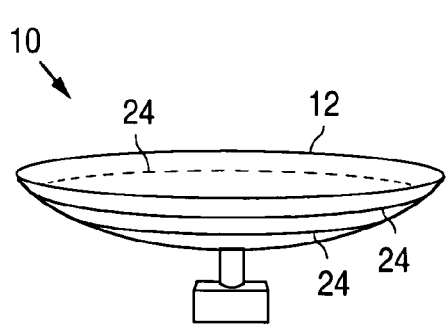
Figure 1C:
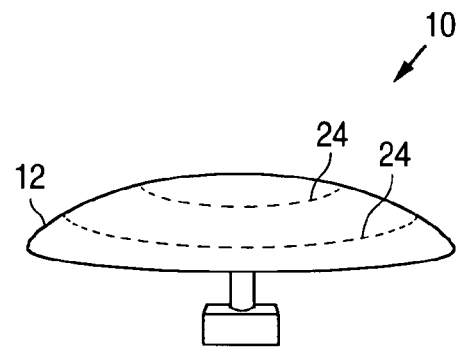
Figure 1D:
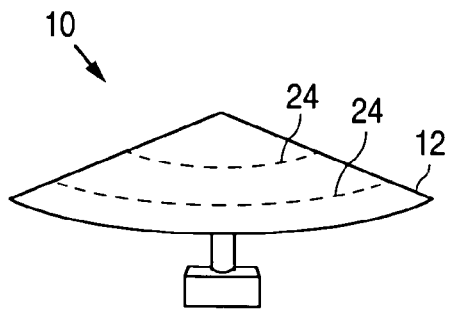
Figure 1E:
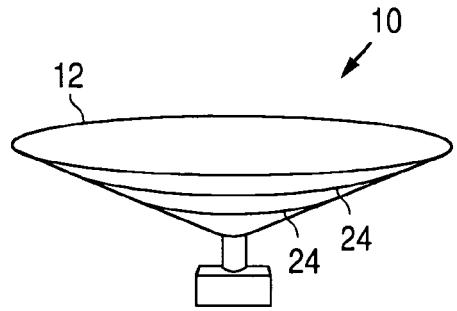

FIGS. 1A–1E illustrate embodiments of an apparatus 10 for coating medical devices, such as stents. Apparatus 10 can include a disk member 12 mounted on a shaft 14. The shaft 14, in turn, can be connected to a motor 16 for rotating the disk member 12 in a clockwise or counterclockwise direction. The disk member 12 can be flat (FIG. 1A), concave (FIG. 1B), convex (FIG. 1C) or conical (FIGS. 1D and 1E) in shape. The disk member 12 can optionally include a lip 18 disposed about the periphery thereof. The lip 18 can extend in an upwardly direction, towards a nozzle 20.

The disk member 12 can be made from any suitable material or can be coated with the desired material so as to minimize the ability of the composition to adhere to a surface 22 of the disk member 12 on which the composition is applied via the nozzle 20. One suitable non-stick surface 22 can be TEFLON. A temperature adjustor 24 can also be provided for adjusting the temperature of the composition during the coating process. The temperature adjustor 24 can be used to increase the temperature of the composition that includes a non-volatile solvent (e.g., dimethylsulfoxide (DMSO), dimethylformamide (DMF), and dimethylacetamide (DMAC)), or alternatively, can be used to decrease the temperature of the composition that includes a volatile solvent. A non-volatile solvent is a solvent that has a vapor pressure less than or equal to about 2.338 MPa (17.54 Torr) at ambient temperature. Should a coating composition be used that has no (i.e., 100% free of solvents) to minimal solvent (e.g., less than about 10% solvent by volume), the temperature adjustor 24 can facilitate placing the polymer in a free flowing fluid form. The temperature adjustor 24 can also be used to increase the temperature to or above the melting temperature of the polymer.

Figure 2A:
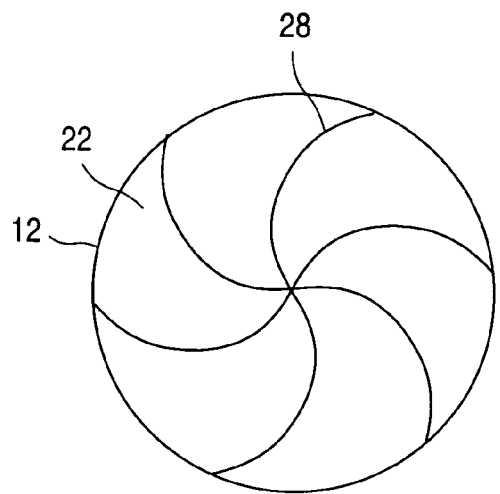
FIGS. 2A–2D illustrate disk members from various embodiments of the apparatus.
Figure 2B:
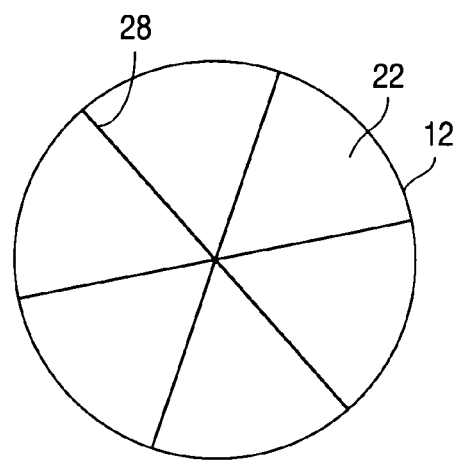
Figure 2C:
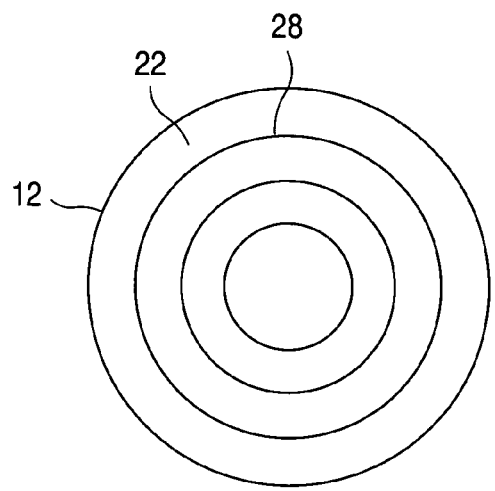
Figure 2D:
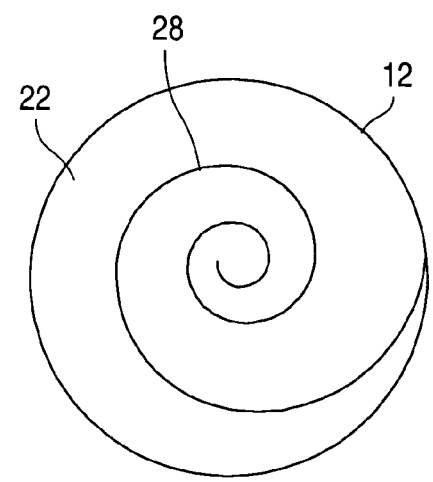

The diameter of the disk can range from about 5.1 cm (2.0 in.) to about 15 cm (6.0 in.), for example about 10 cm (4.0 in.). Referring to FIGS. 2A–2D, grooves or channels 28 can be carved within the surface 22 so as to provide control over the direction of the flow of the composition. FIG. 2A illustrates grooves 28 extending from the center of the disk member 12 to the outer edge of the disk member 12. FIG. 2B illustrates straight grooves 28. FIG. 2C illustrates circular grooves 28 positioned concentrically to one another. The depth and/or width of the grooves 28 can be incrementally smaller as the grooves 28 move closer to the edge of the disk member 12. Yet in another embodiment of the invention, groove 28 can be disposed in a spiral or corkscrew like fashion about the surface 22.

The apparatus 10 can be used for coating any suitable medical substrate that can be implanted in a human or veterinary patient. Examples of such implantable devices include balloon expandable stents, self-expandable stents, stent-grafts, grafts (e.g., aortic grafts), artificial heart valves, cerebrospinal fluid shunts, anastomosis devices, pacemaker electrodes, and endocardial leads (e.g., FINELINE and ENDOTAK, available from Guidant Corporation). The underlying structure of the device can be of virtually any design. The device can be made of a metallic material or an alloy such as, but not limited to, cobalt chromium alloy (ELGILOY), stainless steel (316L), "MP35N," "MP20N," ELASTINITE (nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt; 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention The composition or coating material that can be applied by the nozzle 20 can include a polymer or combination of polymers such as in blend form or conjugated form. The polymer or combination of polymers can be in a liquid state or fluid flow form such as in a melt form. Polymer melt is defined as a polymer or a combination in a non-solid state or having been modified by exposure to temperature equal to or greater than a melting temperature ($T_m$) of the polymer. If a combination of polymers is used, the highest melting temperature must be reached or surpassed. In some embodiments, the composition or coating material is free from any solvents. Free from solvents or solvent free is defined as (1) completely (100%) free from any solvents or (2) having very minimal amount of a solvent(s) including less than 20%, less than 15%, less than 10%, less than 5% or alternatively less than 1% by volume. In some embodiments, the polymer melt is solvent free. For the application of a topcoat layer over polymer-drug layer, the composition can be free from any solvents. In some embodiments, the polymer or the combination can be dissolved in a suitable amount of solvent, for example greater than 50% by volume of a solvent or combination of solvents. In some embodiments, polymeric material can also be emulsified in a solid concentration in a carrier such as water with about 10 weight percent to about 50 weight percent polymeric material.

In some embodiments, a therapeutic substance can be added therein. A therapeutic substance or drug is included in the polymer-drug reservoir layer. If an optional primer layer is applied on the surface of the device, the primer composition should be free from any drugs. However, some drugs may migrate into the primer layer from the reservoir layer. The topcoat layer can be with or without a therapeutic substance. If a therapeutic substance or drug is added to topcoat layer, the drug can be different that the drug used in the polymer-drug layer so as to provide for a cocktail formulation.

Representative examples of polymers that can be used include ethylene vinyl alcohol copolymer (commonly known by the generic name EVOH or by the trade name EVAL), poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D, L-lactic acid); poly(glycolic acid-co-trimethylene carbonate); polyphosphoester; polyphosphoester urethane; poly (amino acids); cyanoacrylates; poly(trimethylene carbonate); poly(iminocarbonate); copoly(ether-esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate;

cellulose; cellulose acetate; cellulose butyrate; cellulose acetate butyrate; cellophane; cellulose nitrate; cellulose propionate; cellulose ethers; and carboxymethyl cellulose.

A solvent can be defined as a liquid substance or composition that is compatible with the polymer and/or drug and is capable of dissolving the polymer and/or drug at the concentration desired in the composition. Examples of solvents include, but are not limited to, dimethylsulfoxide (DMSO), chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methylpyrrolidinone, toluene, and combinations thereof.

The therapeutic substance, drug or active agent can be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which can be appropriate include alpha-interferon, genetically engineered epithelial cells, rapamycin and dexamethasone.

Figure 3:
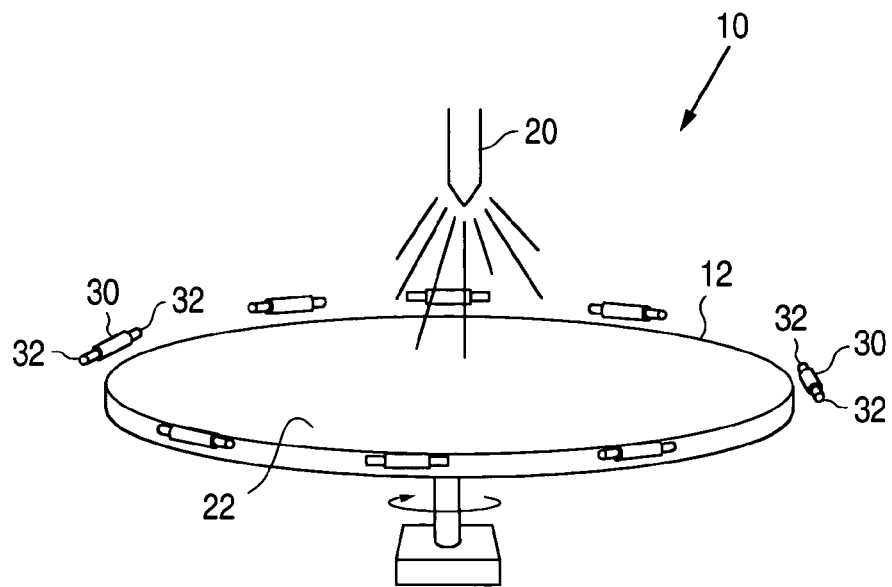
FIG. 3 illustrates an embodiment of the apparatus in use.
Figure 4A:
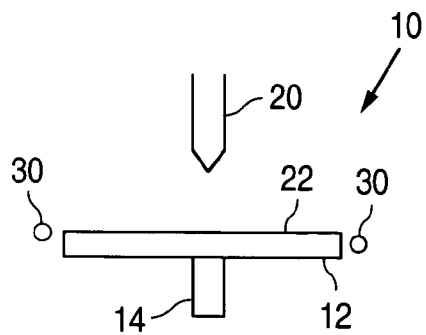
FIGS. 4a and 4b illustrate possible positions of implantable devices with respect to the apparatus.
Figure 4B:
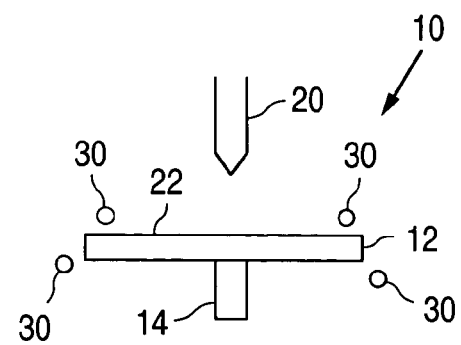

Referring to FIG. 3, a medical device, for example a stent 30, can be positioned in close proximity to the edge of the disk member 12, for example at a distance of about 0.5 mm (0.02 in.) to about 5.0 mm (0.20 in.). For disk member speeds between about 1,000 rpm and about 20,000 rpm, the stent 30 can be placed to the side of the disk member 12, with the longitudinal axis of the stent 30 above or slightly above the surface 22 of the disk member 12, as illustrated in FIG. 4a. For speeds below about 1,000 rpm, the stent 30 should be placed so that the longitudinal axis is below the surface 22, as illustrated in FIG. 4b. For coating stents, the stent 30 can be positioned on a mandrel 32 for rotating the stent 30 about the longitudinal axis of the stent 30. The composition can be applied to the disk member 12 while the disk member 12 is spinning at about 100 rpm to about 20,000 rpm. The flow rate of the from the nozzle 20 can be from about 1.0 g/min. (0.16 lbs./hour) to about 31 g/min. (5.0 lbs./hour). With the use of apparatus 10, the polymer content can be greater than about 80% of the coating material, more narrowly greater than about 90%, in one embodiment greater than about 95%, without the increased viscosity affecting the coating process of the devices. In some embodiments, the coating material can be melt of a polymer (or blend of polymers or chemical bonded polymers) that is solvent free. The solvent free coating or polymer melt application is most suitable with deposition of a topcoat layer to prevent solvent extraction of the drug from the polymer-drug layer. The centripetal force applied to the coating material causes the material to flow off the disk member 12 and onto the stent 30. The temperature of the material can be, for example, about 140° C. to about 240° C., more narrowly about 140° C. to about 200° C., yet more narrowly about 140° C. to about 190° C.

In some embodiments, a primer layer can be formed on the surface of the device. A composition including a polymer an optionally a solvent can be applied to the surface of the device. The composition is free from any drugs. The polymer can be deposited in a liquid state or melt form with the apparatus of the present invention or can alternatively be deposited by conventional techniques such as spraying or dipping. The primer layer should be dried or allowed to solidify before advancing to the application of the reservoir layer. A reservoir composition of a polymer or mixture of polymers and a drug or combination of drugs can be applied to the primer layer or to the surface of the device. The composition can be solvent free such that the polymer is in a free flowing fluid form. The apparatus of the present invention can apply the reservoir composition to the device. In some embodiments, a topcoat can be applied to the dried or solidified reservoir layer. The top coat composition can include a polymer or combination of polymers (e.g., in blend or bonded form) that is in fluid state or a melt form. The composition can be solvent free. The advantages of this formulation of the topcoat include preventing or at least minimizing surface extraction of the drug from the reservoir layer. The amount of solvent in a solvent free coating formulation can be directly correlated to the amount of surface extraction that can occur. Accordingly, the less solvent, the more preferable the formulation for preventing drug extraction. Other advantages of solvent free formulations include prevention of degradation of the drug caused by the solvent; a more predictable drug release rate profile; and the polymer selection would be independent of solubility of the polymer with solvents. Additionally, with the use of solvent-free systems, more polymer can be deposited in a shorter duration of time, therefore increasing manufacturability.

Alternative coating systems and methods that allow for coating materials that are entirely free of any solvents or have relatively little amount of solvent can also be used with the practice of the present invention. For example, a polymer composition can be atomized prior to or subsequent to contact with a carrier gas. The contact can occur under conditions such that vaporization of substantially all of the coating material occurs. The vapor can flow to and condense on the device to form a coating.

Although the invention has been disclosed in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of coating a stent, comprising applying a coating material to a disk member and spinning the disk member about an axis of the disk member such that the force that is applied to the coating material by the disk member discharges the coating material off of the disk member and onto the stent.

2. The method of claim 1, further comprising adjusting the temperature of the disk member to a temperature other than room temperature.

3. The method of claim 1, wherein the surface of the disk member includes grooves for altering the path of the coating material on the surface of the disk member.

4. The method of claim 1, wherein the disk member is flat, conical, or bowl shaped.

5. The method of claim 1, wherein the disk member includes a lip extending in an upwardly direction about the periphery thereof.

6. The method of claim 1, wherein the coating material includes a polymer dissolved in a solvent and optionally a therapeutic substance added thereto.

7. The method of claim 6, wherein the amount of solvent is less than 20% by volume.

8. The method of claim 6, wherein the amount of solvent is less than 15% by volume.

9. The method of claim 6, wherein the amount of solvent is less than 10% by volume.

10. The method of claim 6, wherein the amount of solvent is less than 5% by volume.

11. The method of claim 6, wherein the amount of solvent is less than 1% by volume.

12. The method of claim 1, wherein the coating material is selected from the group consisting of a polymer, or a combination of polymers.

* * * * *